(12) United States Patent
Genix et al.

(10) Patent No.: US 6,467,353 B1
(45) Date of Patent: Oct. 22, 2002

(54) SYSTEM AND METHOD FOR USING A SURROGATE COMPONENT IN SHOCK TESTING

(75) Inventors: Peter D. Genix, Austin, TX (US); Jonathan W. Ellis, Austin, TX (US)

(73) Assignee: Dell Products L.P., Round Rock, TX (US)

(*) Notice: Subject to any disclaimer, the term of this patent is extended or adjusted under 35 U.S.C. 154(b) by 0 days.

(21) Appl. No.: 09/851,297

(22) Filed: May 7, 2001

(51) Int. Cl.[7] .............................................. G01M 7/00
(52) U.S. Cl. .................................... 73/662; 73/1.82
(58) Field of Search ........................ 73/662, 663, 1.82; 361/683, 684, 685

(56) References Cited

U.S. PATENT DOCUMENTS

| | | | |
|---|---|---|---|
| 4,885,707 A | 12/1989 | Nichol et al. | 364/551.01 |
| 5,388,056 A | 2/1995 | Horiuchi et al. | 364/508 |
| 5,513,538 A | 5/1996 | Baker et al. | 73/865.6 |
| 5,631,426 A | 5/1997 | Jao | 73/644 |
| 5,847,259 A | 12/1998 | Hu | 73/1.01 |
| 5,893,048 A | 4/1999 | Pate et al. | 702/56 |
| 5,965,816 A | 10/1999 | Hu | 73/578 |
| 6,021,041 A | 2/2000 | Genix et al. | 361/685 |
| 6,101,432 A * | 8/2000 | Her et al. | 701/29 |

FOREIGN PATENT DOCUMENTS

| | | | |
|---|---|---|---|
| JP | 6186129 | 7/1994 | G01M/7/02 |
| JP | 5010846 | 2/1995 | G01H/1/04 |
| JP | 11142282 | 5/1999 | G01M/7/02 |
| WO | 98/36251 A1 | 8/1998 | G01H/1/00 |
| WO | 99/60351 A1 | 11/1999 | G01H/1/00 |

* cited by examiner

Primary Examiner—Richard A. Moller
(74) Attorney, Agent, or Firm—Baker Botts, L.L.P.

(57) ABSTRACT

A surrogate component for shock testing is disclosed that includes a housing with exterior dimensions, mass, and a center of gravity approximately the same as the exterior dimensions, mass, and center of gravity of a counterpart component. The housing also has a stiffness greater than the counterpart component and has an interface for securing a sensor. In particular, the counterpart component may be hard drive and the housing may be constructed from a molybdenum material.

20 Claims, 6 Drawing Sheets

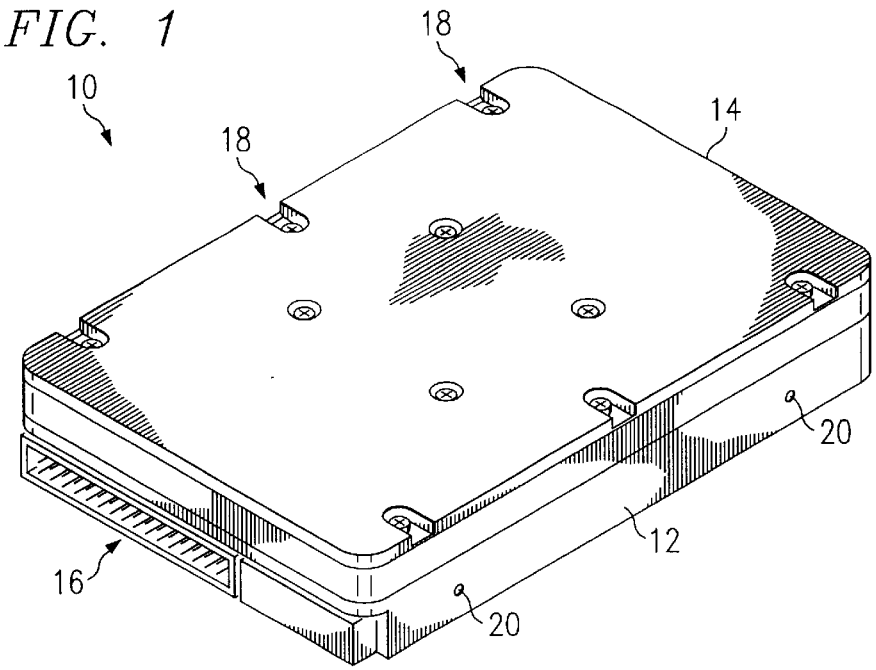
FIG. 1
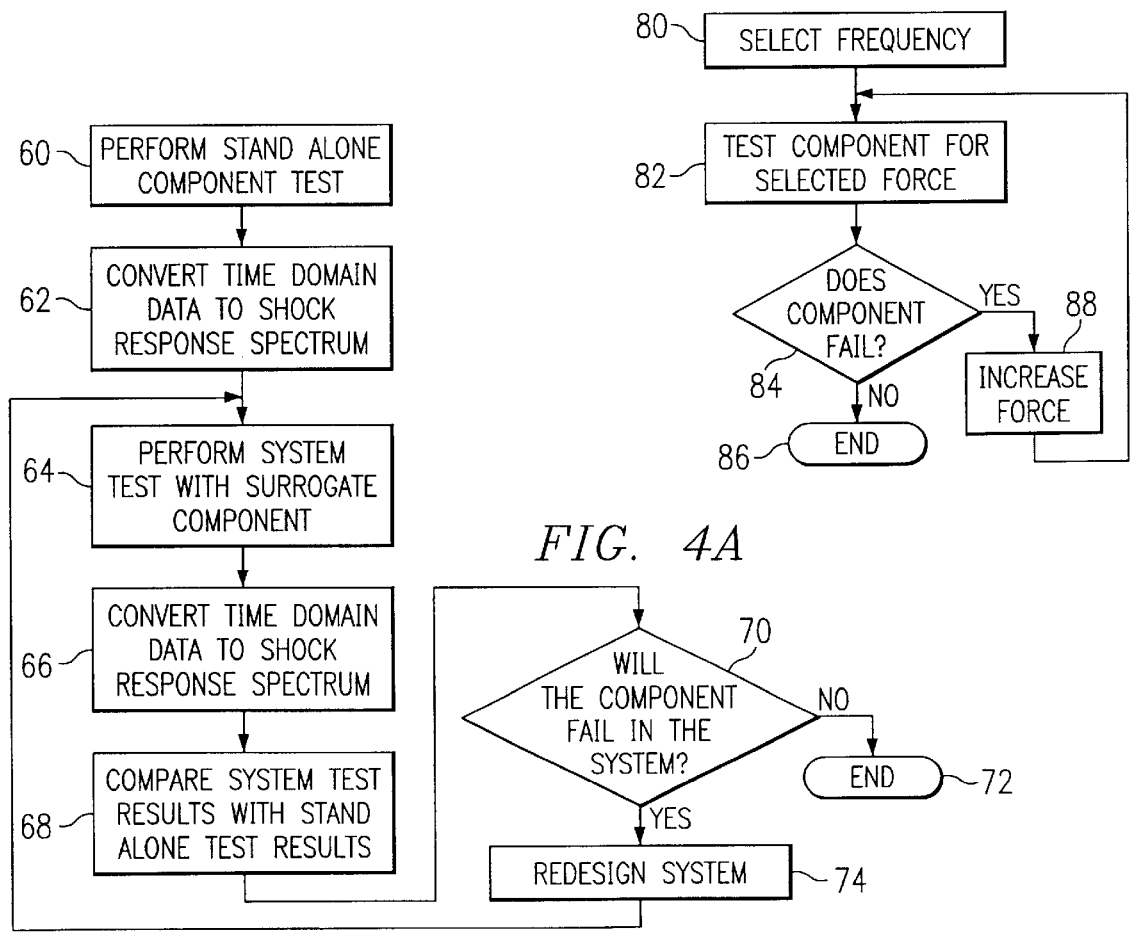
FIG. 4B
FIG. 4A

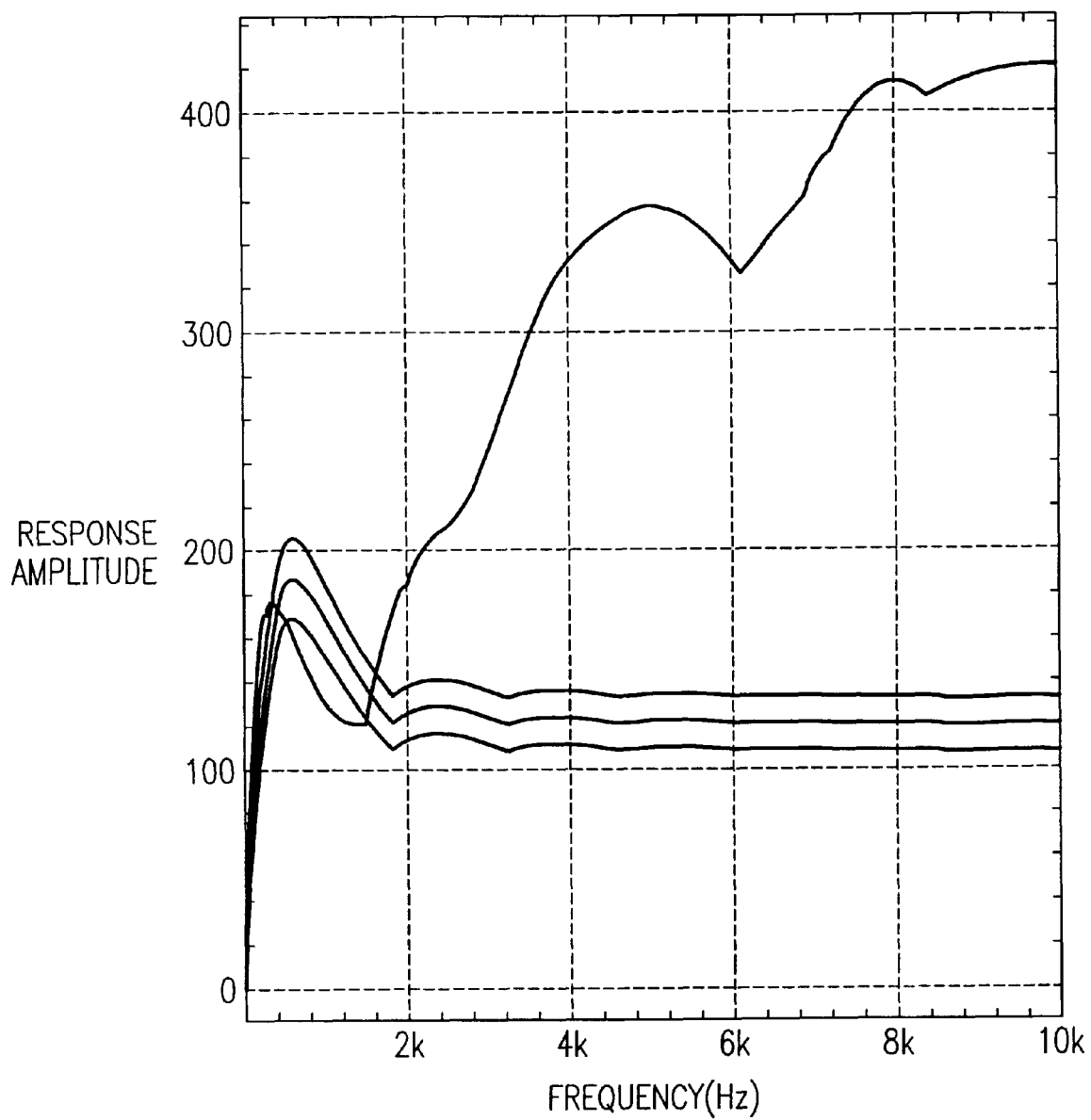

SYSTEM AND METHOD FOR USING A SURROGATE COMPONENT IN SHOCK TESTING

TECHNICAL FIELD

The present disclosure relates in general to the field of electronic devices and more specifically to a system and method for using a surrogate component in shock or vibration testing.

BACKGROUND

Shock and vibration testing is performed on computer systems and system components such as hard drives, liquid crystal displays (LCDs), compact disk (CD) drives, floppy drives, and other peripheral components, in order to determine whether the systems and components can withstand anticipated shock and vibration events. Testing often is performed on assembled systems as well as on individual components. System testing often consists of securing a test system (with components installed within) to a programmable shock table and selectively inducing a desired shock to the system. The force delivered to the system may be measured using an accelerometer.

Testing individual component, which is sometimes referred to as "stand-alone testing" often consists of securing a component to a shock table and delivering a selected shock or vibration to the component. The component is then tested to determine whether the delivered shock or vibration has damaged the component. If the component is undamaged, the selected shock is increase incrementally and the component is re-tested. This process is repeated until the component fails, thereby determining the shock level which a component can withstand. This is sometimes referred to as a component's level of fragility.

The testing of assembled systems presents a number of problems. One problem occurs in the shock testing of systems with installed components. Typically, an accelerometer is secured to a component to measure the shock delivered to the component. This testing is performed in order to determine the shock experienced by a component when the test system experiences a particular shock. However, this measurement is often inaccurate, as the system itself may absorb, dampen, amplify, or otherwise distort the force experienced and recorded by the accelerometer attached to the component. Accordingly, components from different suppliers installed in identical systems may have different responses to the same stimuli delivered to the system.

Also, the component within the test system experiences a complex waveform, as opposed to the ideal waveform experienced by the stand-alone test of the component. The correlation of system level response to the stand-alone response (or device fragility level) is often difficult to make. Part of the problem is from the difficulties that the time domain data presents in comparative analysis. The comparison of complex waveform from the system test to the stand-alone ideal waveform from the stand-alone test is not a direct comparison. Usually the amplitudes of each waveform were compared to determine if the drive in the system had received a shock that exceeded the drive's own fragility established in stand alone testing. In most cases a fundamental waveform cannot be gleaned from this data. There are usually many amplitudes along the time domain of the complex waveform generated by the system test and there is not a reliable way to determine which amplitudes represent sufficient energy to damage a component.

Yet another problem associated with testing components is that system testing may result in component failure, destroying the component. Accordingly, this testing requires significant resource allocation.

SUMMARY

Therefore, a need has arisen for a system and method for comparing the shock response from stand alone component tests and system shock and vibration tests.

A further need has arisen for a system and method for performing shock and vibration testing of systems that reduces resource requirements.

A further need has arisen for a system and method for accurately measuring the shock experienced by a component during system shock and vibration testing.

In accordance with teachings of the present disclosure, a system and method are described for using a surrogate component in shock and vibration testing that substantially reduces the problems and difficulties associated with prior systems and methods for shock and vibration testing of components and systems.

The disclosure includes a surrogate component for shock testing a housing with exterior dimensions, mass, and a center of gravity approximately the same as the exterior dimensions, mass, and center of gravity of a counterpart component. The housing also has a stiffness greater than the counterpart component and has an interface for securing a sensor. More particularly, the counterpart component may be a hard drive and the housing may be constructed from a molybdenum material.

The present disclosure also describes a method for testing a computer system that includes obtaining surrogate component shock data from an accelerometer that is secured to a surrogate component installed within a test system. The surrogate component shock data is then converted to shock response spectrum (SRS) data. The surrogate component SRS data is then compared to SRS data from stand alone counterpart component SRS data.

The present disclosure contains a number of important technical advantages. One technical advantages is converting shock response data into the shock response spectrum. This allows for a meaningful comparison of the shock response from stand alone component tests and system testing.

Another technical advantage of the present disclosure is the introduction of a surrogate component in system testing. The use of a surrogate component reduces resource requirements by eliminating the need to use components which may be damaged during testing. The use of surrogate components also increases the accuracy of the data collected by eliminating the distorting effects of actual components because the increased stiffness of the surrogate component assures that the acceleration measured internally is the same as the acceleration delivered externally to the surrogate component.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 1 is a perspective view of a surrogate component according to the present disclosure;

FIG. 4A is a flow diagram of a method for testing a system using a surrogate component;

FIG. 4B is flow diagram of a method for performing stand alone testing of a component;

FIG. 5F shows SRS data including data outside of he relevant frequency range.

DETAILED DESCRIPTION

Preferred embodiments and their advantages are best understood by reference to FIGS. 1 through 5F, wherein like numbers are used to indicate like and corresponding parts.

Figure 3:
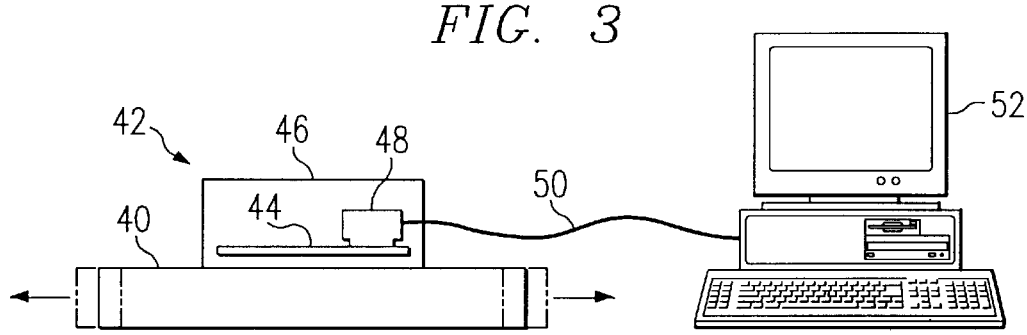
FIG. 3 is a diagram showing a shock testing system.

FIG. 1 is a perspective view of a surrogate component having a housing depicted generally at 10. In the present embodiment, housing 10 include base 12 and top 14 secured by a plurality of removable fasteners 18. Housing 10 further includes mounting interfaces 20 that consist of mounting bores formed to allow housing 10 to be secured to a test system (as shown in FIG. 3). Housing 10 further includes slot 16 formed therein for receiving a ribbon cable.

In the present embodiment, housing 10 has the same approximate exterior dimensions as a counterpart component. In the present embodiment the counterpart component to which housing 10 is modeled after is a hard drive. In an alternative embodiment housing 10 may have the approximate dimensions of any of a number of different hard drives, liquid crystal displays (LCDs), CD drives, DVD drives, floppy drives, or other suitable peripheral components. Housing 10 further has the same approximate mass as the counterpart component it is modeled after. Housing 10 also has the same approximate center of gravity as the counterpart component which it is modeled after.

Housing 10, in the present embodiment, has a stiffness greater than the counterpart component which it is modeled after. In this particular embodiment, housing 10 has stiffness characteristics such that housing 10 experiences its first bending mode at approximately 2300 HZ. The increased stiffness of the housing 10 assures that the acceleration measured internally is the same as the acceleration delivered externally to housing 10. A production level component such as a hard drive does not have this stiffness and is more likely to corrupt or distort the pulse that is delivered to the external surface of the drive and what is received by the accelerometer because the components inside the drive participate in the shock event.

Housing 10 is preferably constructed from a molybdenum material. Alternatively, housing 10 may be constructed from an aluminum material or another suitable material.

Figure 2:
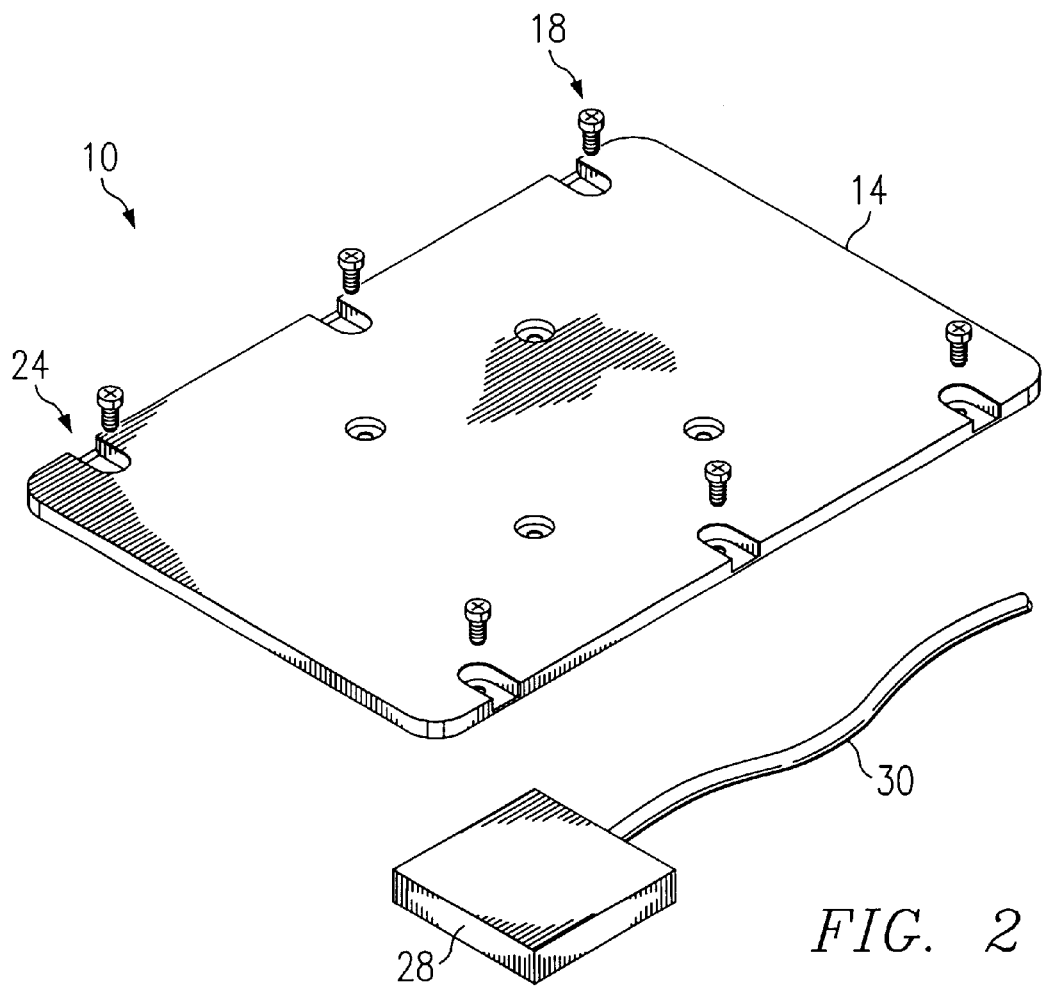
FIG. 2 is an exploded view of a surrogate drive according to the present disclosure, including an accelerometer.
Figure 2:
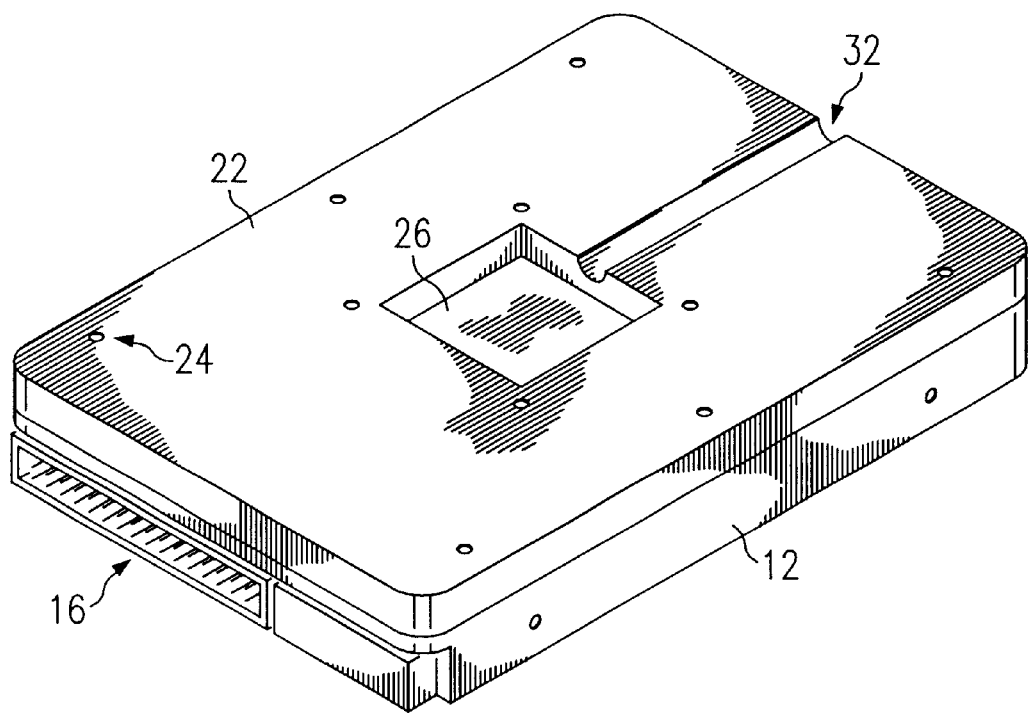

FIG. 2 is an exploded view of the surrogate component shown in FIG. 1. As shown, top 14 may be selectively removed and re-secured to base 12 via the removal and reattachment of fasteners 18 in bores 24 in top 14 and base 12. Bores 24 are preferably formed to receive fasteners 18. Base 12 further includes an interface portion 26 for securing sensor 28. In the present embodiment, interface portion 26 is a cavity formed to receive sensor 28. More specifically, cavity 26 is formed to position sensor 28 in the approximate center of gravity of housing 26.

In the present embodiment, sensor 26 is preferably an accelerometer. More particularly, sensor 26 may be a tri-directional accelerometer with connection 30 connected thereto. Connection 30 may be disposed within slot 32 formed in base 12 when accelerometer 28 is disposed within cavity 26. Accelerometer 28 may be preferably secured within cavity 26 using an adhesive, such as an epoxy resin, a fastener, or any other suitable method for securing accelerometer 28 within cavity 26.

In an alternative embodiment, cavity 26 may be enlarged to allow accelerometer 28 to be selectively located in a plurality of positions within cavity 26. This alternative embodiment would allow, for instance, positioning accelerometer 28 near an edge of housing 10 to allow for the measurement of shock experienced at the edge of housing 10. In another alternative embodiment, cavity 26 may be expanded to allow for a plurality of accelerometers 28 to be disposed therein.

FIG. 3 shows a test system with a surrogate component according to the present disclosure. Test system 42 is secured to shaker table 40. In one particular embodiment, shaker table 40 is a programmable shaker table operable to deliver selected shock and vibration events to systems or components attached thereto.

Test system 42 includes a chassis 46. Motherboard 44 is secured within chassis 46. Surrogate component 48 is preferably secured to motherboard 44. Surrogate component 48 (and the sensor associated with surrogate component 48, as shown in FIG. 2) is preferably operatively connected to digital computer 52 via connection 50. Digital computer 52 is operable to receive and record data received from surrogate component 48. More particularly, digital computer 52 is preferably operable to record time domain data from digital computer 52 and is operable to convert data received and recorded from surrogate component as time domain data into frequency domain data or so-called shock response spectrum (SRS) data. In an alternative embodiment, more than one component may be installed within test system 42. Also in an alternative embodiment, digital computer 52 may be any suitable system for receiving and recording data received from surrogate component 48.

Figure 5A:
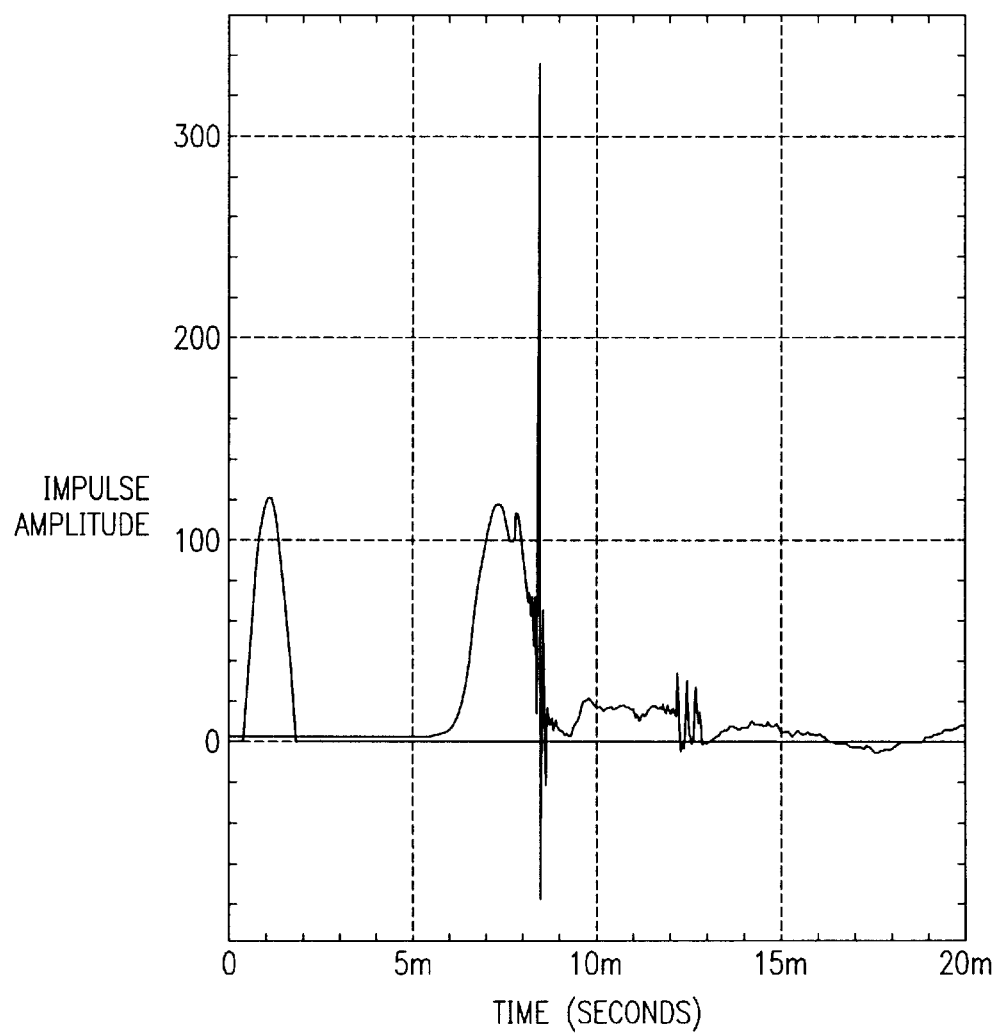
FIG. 5A shows response data in the time domain.
Figure 5B:
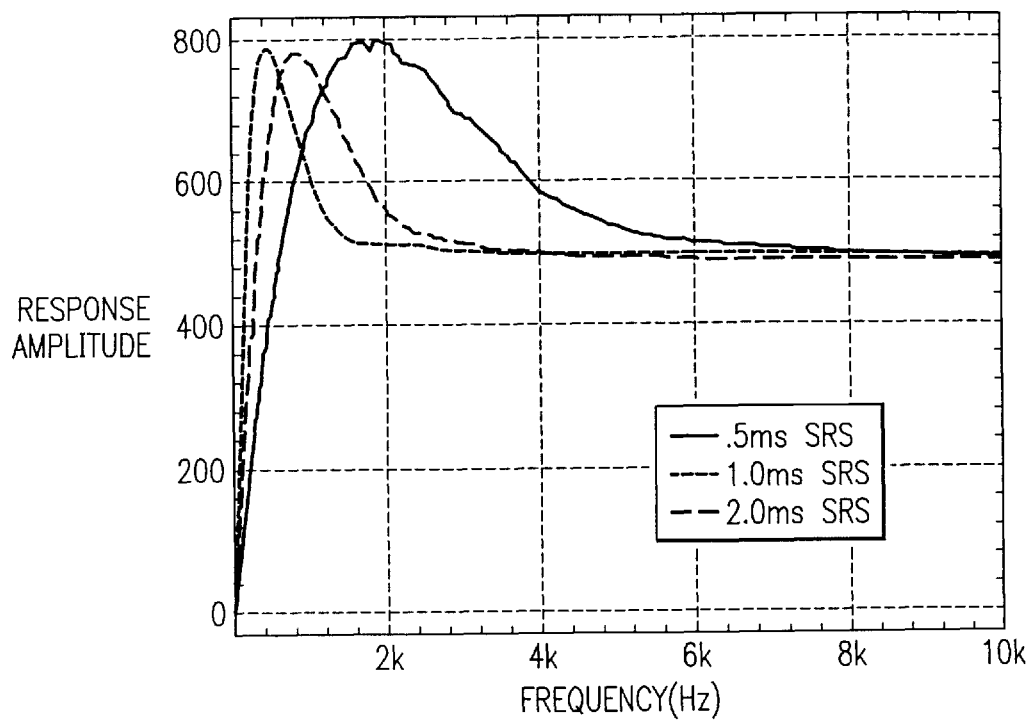
FIG. 5B shows SRS data from stand alone testing of a component.

FIG. 4A is a flow diagram of a method for testing a system using a surrogate component. The method includes performing a stand alone test of a component 60. Preferably, this testing takes place with a component such as a hard drive secured to the shock table and is used to determine the component's level of fragility. Multiple stand alone component tests may be performed on a single type of component to ensure the accuracy of the testing. The data is preferably recorded from the testing that is in the time domain. Data may be recorded either from a sensor associated with the shock table or from a sensor associated with the component being tested. After time domain data has been recorded, the time domain data is preferably converted into SRS data using known techniques such as a Zonic Medallion (time domain) to Signalysis SRS-type conversion. An example of time domain data converted into SRS data is shown in FIG. 5B which shows SRS data for a series of three tests of a component. The peak amplitude shown in the SRS data represents the components fragility level.

After performing stand alone tests on components, system tests may be preferably performed on test systems with surrogate components installed therein 64 and as shown in FIG. 3. Preferably, the surrogate components are modeled after the components tested in step 60, which may also be called the "counterpart component" of the surrogate component. The modeling of the counterpart components is further preferably directed at approximately emulating the exterior dimensions, mass, and center of gravity of the counterpart components.

Figure 5C:
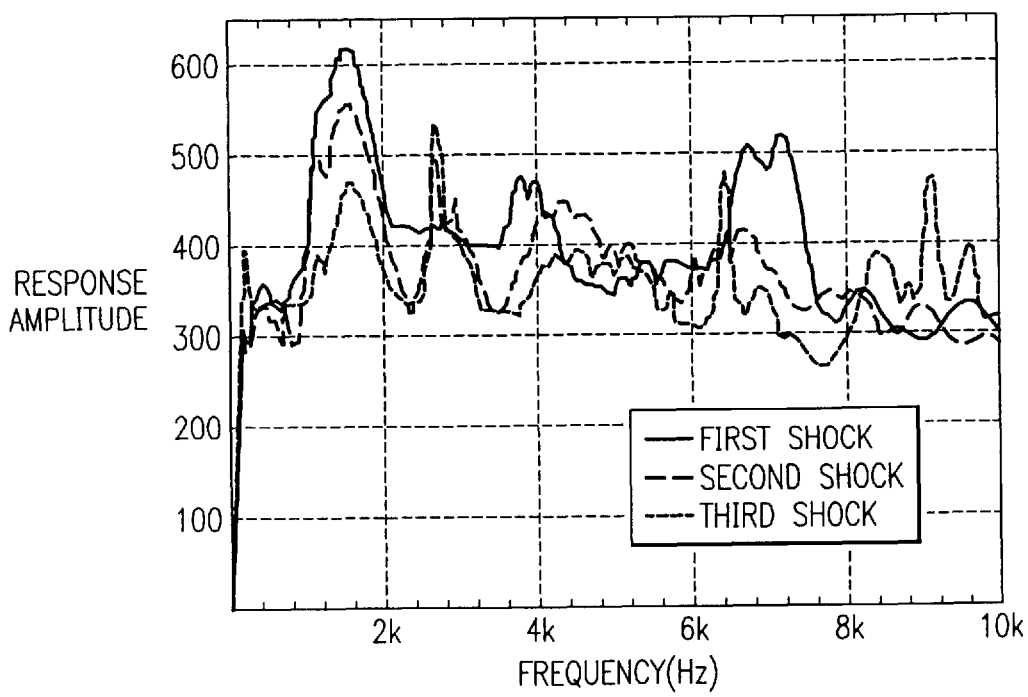
FIG. 5C shows response data from a system test.

The system test is preferably performed to simulate expected shock or vibration events anticipated to effect a system. Test data is recorded from the system test during and is then preferably converted into SRS data 66. An example of the type of data recorded is shown in FIG. 5A, showing response data in the time domain. An example of converted SRS data is shown in FIG. 5C.

Figure 5D:
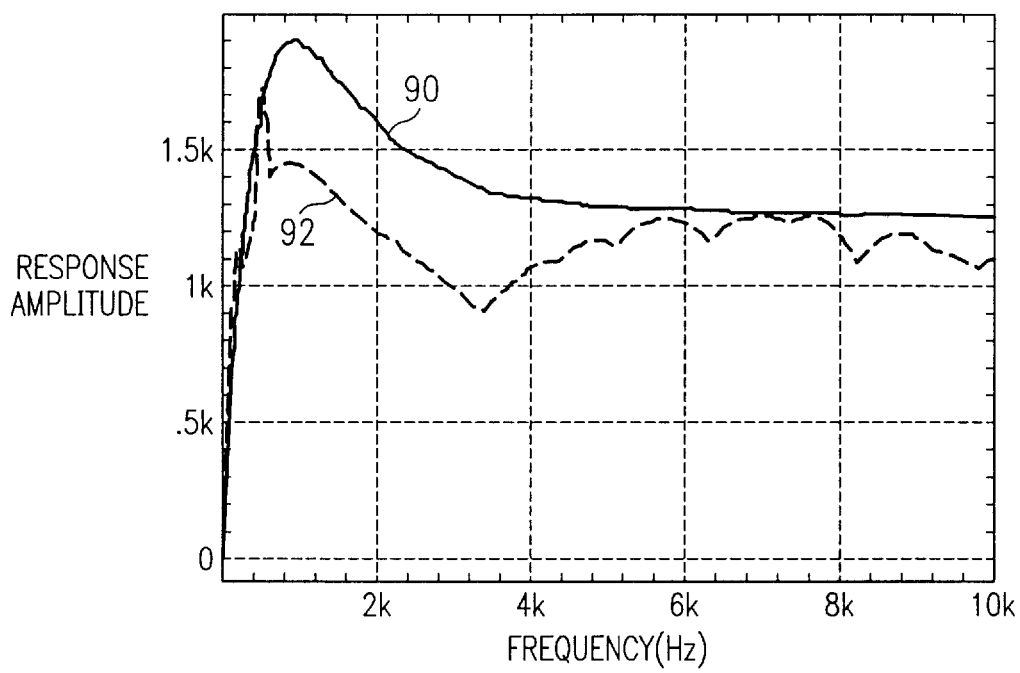
FIG. 5D shows a comparison of stand alone SRS test data and system SRS test data.
Figure 5E:
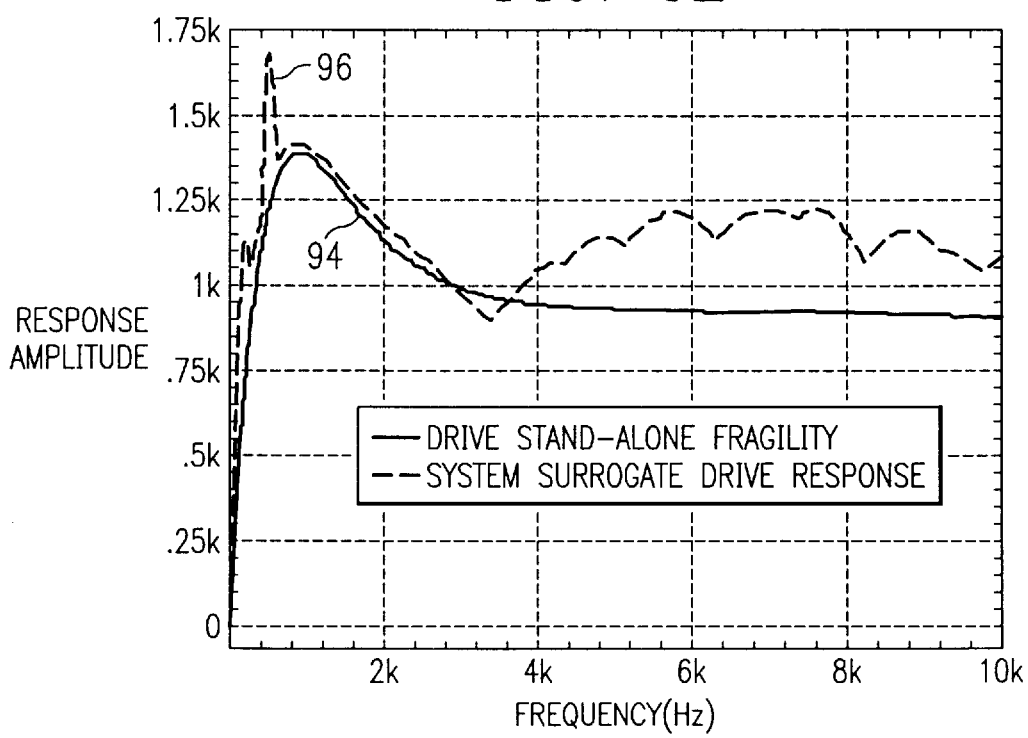
FIG. 5E shows a comparison of stand alone SRS test data and system SRS test data.

After obtaining SRS data from both stand alone tests of components and test systems, the SRS data of the tests is compared 68. This comparison is preferably made to determine whether the component will experience a shock within the system that is greater than its fragility level 70. Examples of such a comparison are shown in FIG. 5D and FIG. 5E. FIG. 5D is a comparison of SRS data from a stand-alone test 90 and SRS data from a system test 92. FIG. 5D shows that the SRS system test data 92 does not exceed the fragility level of stand-alone test data 90. Accordingly the component tested is not anticipated to fail and testing is complete 72.

FIG. 5E is also a comparison of SRS data from a stand-alone test 94 and SRS data from a system test 96. However, in this example, the SRS system test data 96 exceeds the fragility level of stand-alone test data 94. Accordingly the component tested is anticipated to fail. Because the component is expected to fail during anticipated shock events, the system may be redesigned to prevent such events or a component with a greater level of fragility may be implemented within the system 74.

It should also be noted that experience has shown that data outside of an expected frequency range may sometimes by disregarded in the comparative analysis of system SRS data and stand-alone SRS data. FIG. 5F is an example of test data in which some of the amplitude data at higher frequencies may be disregarded because the component is not anticipated to be effected by forces acting at these frequencies.

FIG. 4B is flow diagram of a method for performing stand alone testing of a component. The method includes first selecting a frequency for testing 80 and then proceeding with a stand-alone test of a component at a given force 82. Preferably, the intial force selected is a relatively low force, which the component is anticipated to withstand. After the test is performed, the component is tested to determine whether the component has failed 84. If the component has not failed, the selected force may be increased incrementally and the test may be performed again 82. After each test, the component is tested to determine whether the component has been damaged 84. This process continues and the selected force is repeated until the component fails 86. Further, the entire process may be repeated for alternative frequencies 80.

Although the disclosed embodiments have been described in detail, it should be understood that various changes, substitutions and alterations can be made to the embodiments without departing from their spirit and scope.

What is claimed is:

1. A surrogate component for shock testing comprising:
    a housing having exterior dimensions, mass, and center of gravity approximately the same as the exterior dimensions, mass, and center of gravity of a counterpart component;
    the housing having a stiffness greater than the counterpart component; and
    the housing having an interface operable to secure a sensor.

2. The surrogate component of claim 1 wherein the housing further comprises:
    a base having a cavity formed therein for securing the sensor; and
    a top selectively removable from the base.

3. The surrogate component of claim 2 wherein the cavity further comprises a cavity formed to position the sensor at approximately the center of gravity of the housing.

4. The surrogate component of claim 2 wherein the cavity further comprises a cavity formed to facilitate the positioning of the sensor in a plurality of locations within the cavity relative to the geometric center of the housing.

5. The surrogate component of claim 1 wherein the housing is comprised of a molybdenum material.

6. The surrogate component of claim 1 wherein the housing is comprised of an aluminum material.

7. The surrogate component of claim 1 wherein the counterpart component further comprises a hard drive.

8. The surrogate component of claim 1 wherein the counterpart component further comprises a liquid crystal display.

9. The surrogate component of claim 1 wherein the counterpart component further comprises a compact disk drive.

10. The surrogate component of claim 1 wherein the counterpart component further comprises a floppy drive.

11. The surrogate component of claim 1 wherein the sensor comprises at least one accelerometer.

12. The surrogate component of claim 1 wherein the sensor further comprises at least one tri-directional accelerometer.

13. A system for shock testing comprising:
    a shock table;
    a test system secured to the shock table;
    at least one surrogate component installed within the test system, the surrogate component comprising:
        a housing having exterior dimensions, mass, and center of gravity approximately the same as a counterpart component;
        the housing having a stiffness greater than the counterpart component;
        the housing having a cavity formed therein;
        an accelerometer secured within the cavity; and
    a computer operatively coupled to the accelerometer, the digital computer operable to receive and record surrogate component shock data from the accelerometer.

14. The system of claim 13 further comprising the computer operable to convert the recorded information into shock response spectrum (SRS) data.

15. The system of claim 13 wherein the counterpart component further comprises a hard drive.

16. The system of claim 13 wherein the housing comprises a molybdenum material.

17. A method for testing a computer system comprising:
    obtaining surrogate component shock data from an accelerometer secured to a surrogate component installed within a test system;
    converting the surrogate component shock data to the shock response spectrum (SRS); and
    comparing the surrogate component SRS data to known counterpart component SRS data.

18. The method of claim 17 further comprising:
    performing stand alone shock testing of the counterpart component at a given force;

obtaining counterpart component shock data from an accelerometer secured to the counterpart component;

repeating the shock testing of the counterpart component at increasing force until counterpart component failure; and converting the counterpart component shock data to SRS data.

19. The method of claim 17 further comprising redesigning the test system after determining that the surrogate component SRS data is greater than the counterpart component SRS data.

20. The method of claim 17 wherein comparing the surrogate component SRS data to known counterpart component SRS data further comprises considering the relevant frequency range of the surrogate component SRS data and the counterpart component SRS data.

* * * * *